US008973189B2

United States Patent
Wilson et al.

(10) Patent No.: US 8,973,189 B2
(45) Date of Patent: Mar. 10, 2015

(54) PATIENT POSITIONING DEVICE FOR STEREOTACTIC RADIOSURGERY

(71) Applicant: Medtec, Inc., Orange City, IA (US)

(72) Inventors: Roger F. Wilson, Sarasota, FL (US); Willet F. Whitmore, III, Longboat Key, FL (US); Bruce Ribble, Swisher, IA (US)

(73) Assignee: Medtec, Inc., Orange City, IA (US)

( * ) Notice: Subject to any disclaimer, the term of this patent is extended or adjusted under 35 U.S.C. 154(b) by 0 days.

(21) Appl. No.: 14/058,608

(22) Filed: Oct. 21, 2013

(65) Prior Publication Data

US 2014/0115786 A1    May 1, 2014

Related U.S. Application Data

(60) Provisional application No. 61/718,903, filed on Oct. 26, 2012.

(51) Int. Cl.
*A61G 13/12* (2006.01)
*A61B 19/00* (2006.01)

(52) U.S. Cl.
CPC ............ *A61G 13/121* (2013.01); *A61B 19/203* (2013.01); *A61B 2019/204* (2013.01)
USPC ........................ 5/622; 5/621; 5/650; 128/845

(58) Field of Classification Search
USPC ...................... 5/622, 601, 621, 624, 640, 650; 128/845
See application file for complete search history.

(56) References Cited

U.S. PATENT DOCUMENTS

| 4,465,069 | A | 8/1984 | Barbier et al. | |
|---|---|---|---|---|
| 5,549,616 | A | 8/1996 | Schulte et al. | |
| 8,146,599 | B2 | 4/2012 | Wilson et al. | |
| 8,172,189 | B2 | 5/2012 | Wilson et al. | |
| 2006/0225213 | A1* | 10/2006 | Tomcany | 5/622 |
| 2008/0163426 | A1* | 7/2008 | Tomcany | 5/622 |
| 2009/0308400 | A1 | 12/2009 | Wilson et al. | |
| 2014/0059771 | A1* | 3/2014 | Schuele et al. | 5/622 |
| 2014/0096322 | A1* | 4/2014 | Farag et al. | 5/622 |

OTHER PUBLICATIONS

International Search Report for PCT/US2013/065189 mailed Jan. 15, 2014.

* cited by examiner

*Primary Examiner* — Peter M Cuomo
*Assistant Examiner* — Brittany Wilson
(74) *Attorney, Agent, or Firm* — Caesar, Rivise, Bernstein, Cohen & Pokotilow, Ltd.

(57) ABSTRACT

A device for positioning and immobilizing the head of patient on a treatment table is disclosed. The device comprises a bridge member, a longitudinal arm, and two transverse arms. The bridge member is releasably mounted on the treatment table. The longitudinal arm is pivotably coupled to the upper portion of the bridge member and is arranged to be pivoted from one side of the bridge member to the other side of it, and vice versa, above the patient's head. The transverse arms are releasably secured to the longitudinal arm and are positionable along a portion of the length of the longitudinal arm. Each transverse arm is rotatable about its longitudinal axis and mounts an anatomy engagement component, e.g., a nasion pad or a bite tray, thereon which can be moved into engagement with the patient's head.

22 Claims, 8 Drawing Sheets

PATIENT POSITIONING DEVICE FOR STEREOTACTIC RADIOSURGERY

CROSS-REFERENCE TO RELATED APPLICATIONS

This utility application claims the benefit under 35 U.S.C. §119(e) of Provisional Application Ser. No. 61/718,903 filed on Oct. 26, 2012 entitled Patient Positioning Device for Stereotactic Radiosurgery. The entire disclosure of this provisional application is incorporated by reference herein.

STATEMENT REGARDING FEDERALLY SPONSORED RESEARCH OR DEVELOPMENT

"Not Applicable"

INCORPORATION-BY-REFERENCE OF MATERIAL SUBMITTED ON A COMPACT DISK

"Not Applicable"

FIELD OF THE INVENTION

This invention relates generally to holding devices and more particularly for systems for positioning and immobilizing the head of a patient on a treatment couch or other patient support structure for stereotactic radiosurgery.

BACKGROUND OF THE INVENTION

Stereotactic radiosurgery (SRS) is a common treatment modality for brain tumors and typically involves repeated doses of radiation provided to the patient over a period of time. In order to ensure that the radiation is directed to the precise target it is a common practice to make use of a positioning/fixation device to hold the patient's head in a desired, immobilized position. Since that device will be used repeatedly it is typically adjustable so that the various portions of it are in desired positions/orientations to accommodate the particular anatomy of the patient's head. Head position/fixation devices are currently available from various manufacturers. Civco Medical Solutions (hereinafter "CIVCO") is one such manufacturer.

While the commercially available devices to hold the head of a patient immobilized, including those commercially available from CIVCO, are generally suitable for their intended purposes such devices tend to be rather complicated in structure and not ideally suited for ease of assembly and adjustment. For example, the commercially available devices from CIVCO make use of an arch or bridge member which is mounted on the couchtop (or other patient support surface) and spans the head of the patient from one side of the patient's head to the other, i.e., one leg of the arch is disposed on the left side of the patient's head, with the other leg of the arch being disposed on the right side of the patient's head. The upper portion of the arch, which bridges its two legs is arranged to mount components which are arranged to engage portions of the patient head to immobilize the patient's head. One such component is a so-called "nasion" pad, which is a silicone pad arranged to engage the nose of the patient. Another component is a bite tray which is arranged to be inserted into the patient's mouth and held between the patient's teeth. The mounting of the nasion pad and the bite tray on the arch of the CIVCO device is accomplished by means of a single long, horizontally extending arm. That long arm is arranged to be located at the upper portion of the bridge adjacent either the right side leg of the arch or the left side leg of the arch so that it extends above and parallel to the right or left side, respectively, of the patient's head. A pair of shorter transverse arm are mounted on the long arm and arranged to be positioned at various longitudinal positions therealong to accommodate particular anatomy of the patient's head. One of the transverse arms mounts the nasion pad, while the other mounts the bite tray. The nasion pad and the bite tray can be mounted on either the superior or inferior side of the transversely extending arms. Moreover, each of the transversely extending arms is arranged to be rotated about a horizontal axis so that the particular component held by it is at a desired angular orientation with respect to the underlying patient's head.

In order to provide additional space between the transverse arms and the couchtop for the patient's head, without extending the height of the arch, the CIVCO device makes use of transverse arms that are constructed so that their respective distal ends, which extend parallel to the plane of the couchtop, are offset vertically from the axes of rotation of those arms. Thus, the distal end of each transverse arm is above the axis about which the arm is rotated to provide more space below to accommodate the patient's head.

As mentioned above, and in the interest of best fitting the device to the anatomy of the particular patient, the long (longitudinally extending) arm can be positioned at one of two positions on the arch, i.e., a left side position or a right side position. Thus, for example, if the mounting of the long arm on the one side (e.g., the left side) of the arch is not desired or appropriate, and mounting on the other side (e.g., the right side) is preferred, the long arm with the transverse arms mounted thereon can be disconnected from the arch and moved to the new desired position. However, such action is a somewhat complicated procedure and risks dropping or misplacement of portions of the disassembled device.

Accordingly, a need exists for a SRS positioning/immobilization device which enables the positioning of the longitudinal (long) arm, with the transverse (short) arms mounted thereon, to be readily moved (pivoted) to either the right side of the arch or the left side of the arch without disassembling the device, and in a manner ensuring that the longitudinal arm is in the precise orientation in that desired right or left mounting position. In addition, a need exists for a device having mechanisms to adjust the position of the transverse arms at any position along the length of the longitudinal arm and lock it in place therein, while also enabling the rotation of the transverse arm about its rotational axis so that its angular orientation can be readily adjusted, set and locked in place with a single knob and without requiring removal of the transverse arms from the longitudinal arm. Further still, a need exists for a device which enables the components mounting the nasion pad and the bite tray (or any other anatomy engagement components) on their respective transverse arms to be readily disposed on either the superior or inferior side of each arm and to be readily adjusted vertically and locked in place thereat. Further yet, a need exists for a device which provides indicia indicating the appropriate position of the various components of the device, so that the device can be reused to reset the components to previously defined positions, thereby ensuring that the device can be used to immobilize the patient's head during repeated treatments. Still further yet, a need exists for a device which facilitates the mounting and securement of the device on the couchtop or a support base in a very simple, one step operation.

The subject invention addresses those needs.

All references cited and/or identified herein are specifically incorporated by reference herein.

SUMMARY OF THE INVENTION

In accordance with one aspect of the invention there is provided a device for positioning and immobilizing the head of patient on a treatment table for some type of therapy that is to be repeated. The device comprises a bridge member, a first arm, and at least a second arm (e.g., a second and third arm). The bridge member is arranged to be mounted on the treatment table and has an upper portion extending transversely across the head of the patient. The first arm is an elongated member pivotably coupled to the upper portion of the bridge member and which projects longitudinally and above the patient's head. The first arm is arranged to be pivoted from one side of the upper portion of the bridge member to the other side of the upper portion of the bridge member, and vice versa, whereupon the first arm can be located longitudinally above either side of the patient's head on the treatment table. The second arm is an elongated member releasably secured to the first arm to extend transversely to the longitudinal (first) arm and is positionable along a portion of the length of the first arm and arranged to mount an anatomy engagement component, e.g., a nasion pad or a bite tray, for engaging a portion of the anatomy of the patient's head.

In accordance with a preferred exemplary embodiment of the invention the device includes two transverse arms, one arranged for mounting a nasion pad and the other for mounting a bite tray. The longitudinal arm includes a longitudinal axis and each of the transverse arms includes a respective longitudinal axis. Each transverse arm is arranged to be rotatable about its longitudinal axis, which axis is perpendicular to the first axis of the first (longitudinal) arm to orient the anatomy engagement component mounted thereon at a precise angular orientation with respect to the treatment table. The mounting of the anatomy engagement components on the respective transverse arms is achieved by means of respective subassemblies, each of which is positionable along a portion of the length of the transverse arm on which it is mounted. Moreover, each subassembly is also positionable on its transverse arm toward and away from the treatment table. Further still, the transverse arms are constructed so that the subassemblies mounting the anatomy engagement components can be readily mounted on either the superior side surface or the inferior side surface of the transverse arm by merely sliding the subassembly off the free end of the transverse arm. Indicia are provided on the longitudinal arms to indicate the precise position of the transverse arms with respect thereto. Indicia are provided on the transverse arms to indicate the position of the subassemblies mounting the anatomy engagement components along the transverse arms and also indicate on which surface (superior or inferior) the subassembly is mounted.

DETAILED DESCRIPTION OF THE PREFERRED EMBODIMENT

Figure 1:
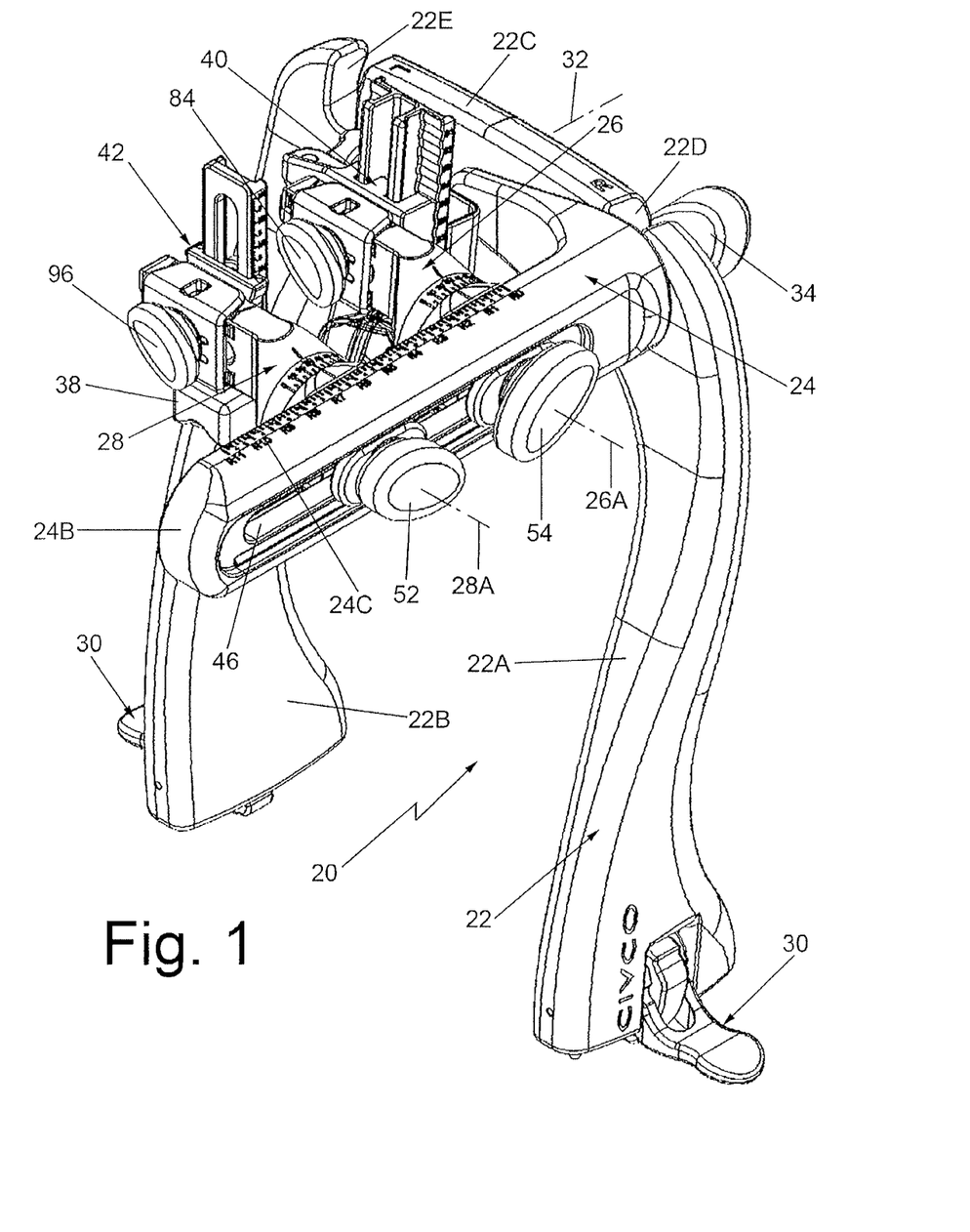
FIG. 1 is an isometric view of a device constructed in accordance with this invention for positioning and immobilizing the head of a patient on a treatment table, couch or other patient support structure for stereotactic radiosurgery, with the portion of the device, i.e., the longitudinally extending arm on which a pair of transversely extending arms are mounted, oriented on the right side of the device and with the anatomy engaging components of the device facing downward as they would be when used to position and immobilize the head of the patient.

Referring now to the various figures of the drawing wherein like reference characters refer to like parts, there is shown in FIG. 1 a device 20 for use on a conventional treatment table 12 (FIG. 6), couchtop, or other patient support panel (not shown) to enable the repeatedly positioning and immobilization (fixation) of the patient's head for SBS. To that end the device 20 basically comprises a bridge or arch member 22, a first longitudinally extending long arm 24, a second transversely extending short arm 26 and a third transversely extending short arm 28. The bridge member 22 is of an arch-like construction which includes a pair of legs 22A and 22B and an upper section 22C connecting the upper ends of the legs. Each of the legs includes a latch mechanism 30 (to be described later) at its lower end to releasably secure the associated leg to an associated slot 10 (FIG. 6) formed in the treatment table 12.

The components forming the device 20 are formed of any suitable conventional materials use for stereotactic devices.

Figure 2:
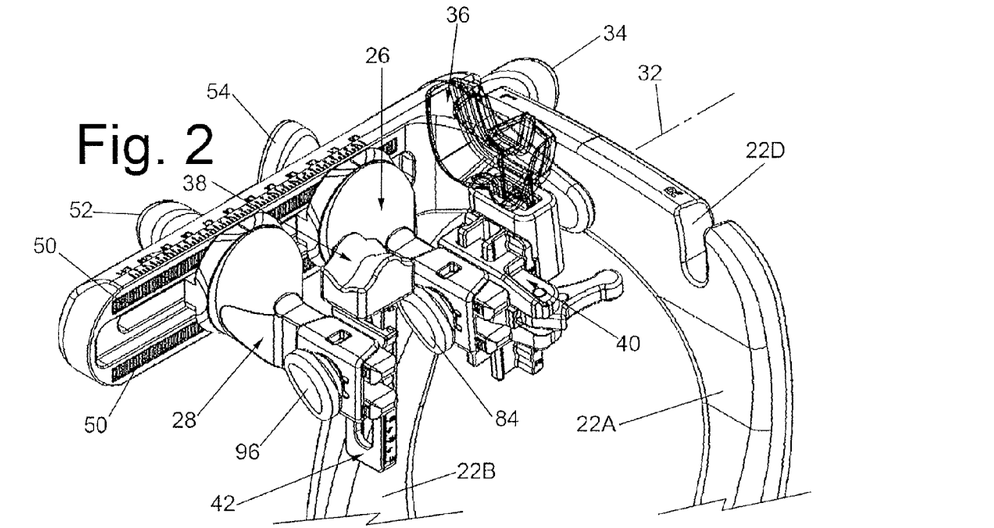
FIG. 2 is an isometric view of the upper portion of the device shown in FIG. 1, but showing the device with its longitudinally extending arm oriented on the left side of the device and with the anatomy engaging components facing upward to facilitate their mounting and adjustment.
Figure 3:
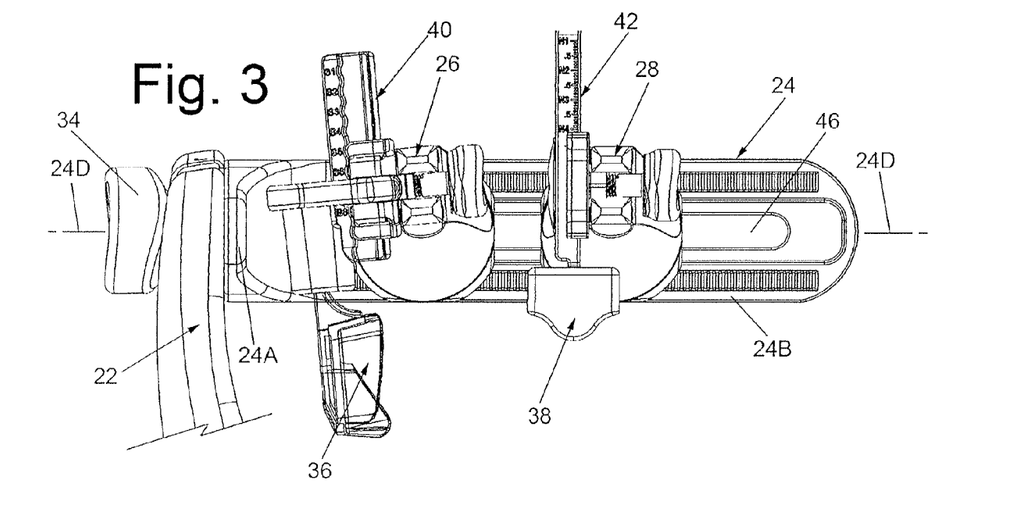
FIG. 3 is a side view of the upper portion device of the device like shown in FIG. 1, but with the patient engaging components, i.e., a nasion pad and a bite tray (which are mounted on the transversely extending arms) directed downward as they would be when positioning and immobilizing the head of the patient.
Figure 4:
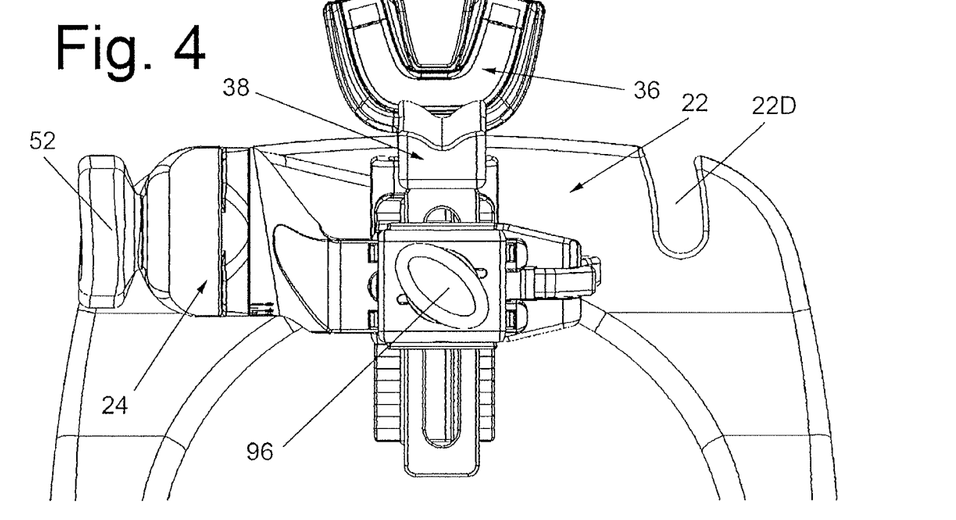
FIG. 4 is a front view of the upper portion of the device when it is in the state shown in FIG. 2.
Figure 5:
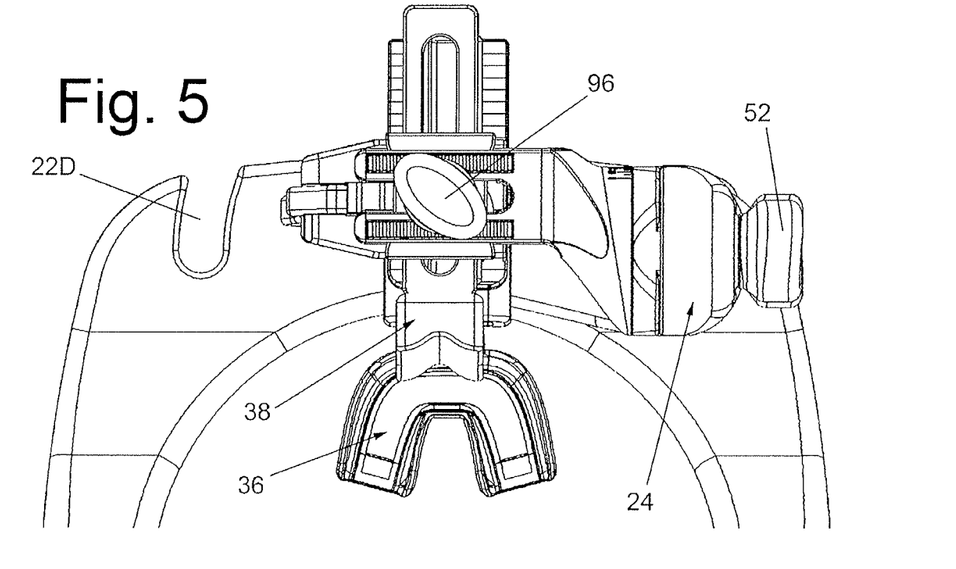
FIG. 5 is a front view of the upper portion of the device when it is in the state shown in FIG. 3.
Figures 6, 7, 8:
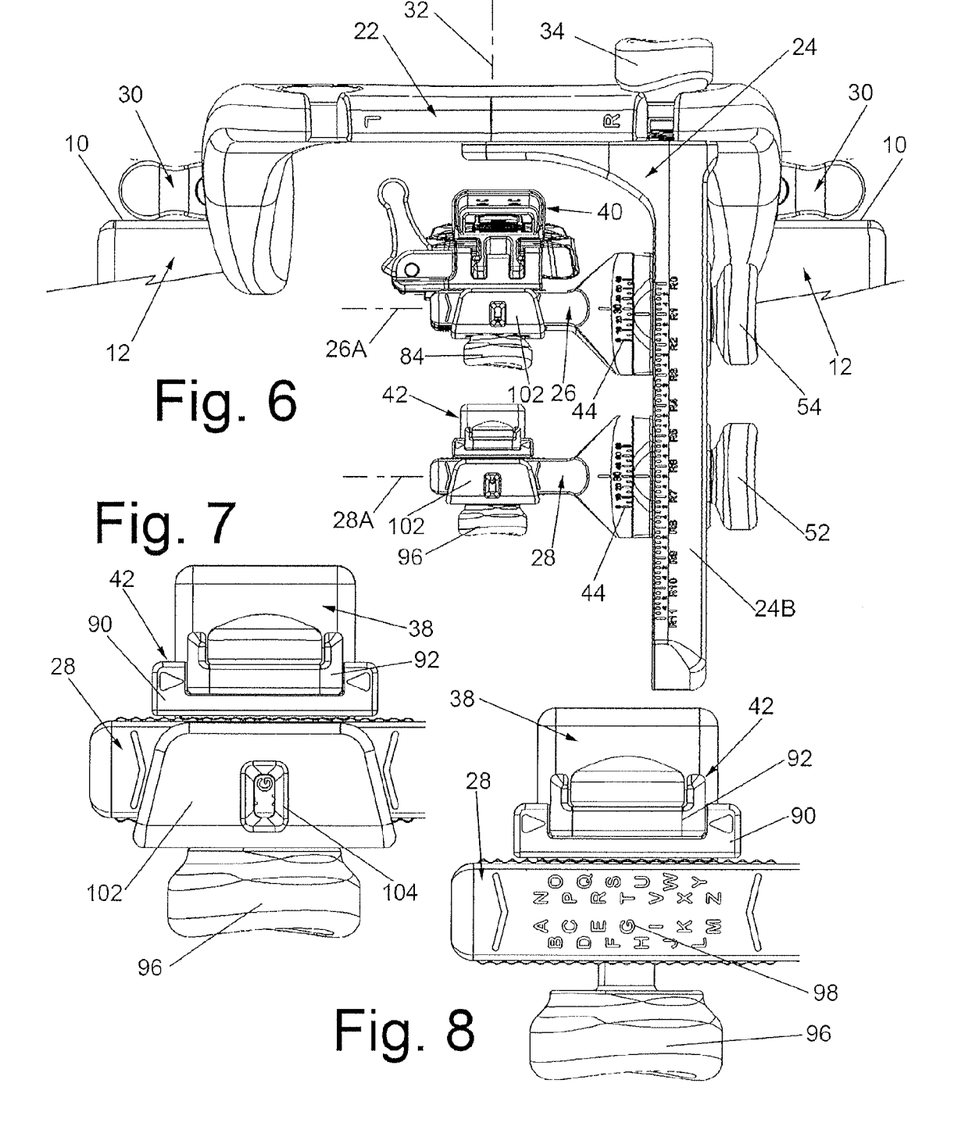
FIG. 6 is a reduced top view of the device shown in FIG. 1 shown mounted on a treatment table or base.
FIG. 7 is an enlarged top view of a portion of the transversely extending arm and the subassembly mounting the nasion pad thereon for providing an indication of the position of the subassembly on that arm.
FIG. 8 is a top view similar to that of FIG. 7 but with one of the components of the subassembly removed.

As best seen in FIGS. 1, 3 and 6, the long arm 24 is a generally L-shaped integral member having a base portion 24A and an extending portion 24B. The extending portion 24B is an elongated, linear member having a longitudinal axis 24D (FIG. 3). The base portion 24A is pivotably connected to the center of upper portion 22C of the bridge via a pivot joint thereat so that the arm 24 can pivot about a pivot axis 32 (FIG. 1) so that the extending portion 24B of the arm will be located on either the left or right side of the bridge member and disposed generally parallel to and above the plane of the treatment table or couchtop. To that end, the upper section of the bridge on the right side thereof and adjacent the leg 22A includes a slot 22D for receipt of a knob 34 (to be described later) connected to the arm 24 at the junction of the base portion 24A and extending portion 24B when the arm 24 is in its right position, such as shown in FIG. 1. The upper portion of the bridge adjacent the slot 22D includes the indicium "R" adjacent to the slot to indicate the right position for the arm 24. In a similar manner the upper section of the bridge on the left side thereof adjacent the leg 22B includes a slot 22E for receipt of the knob 34 when the arm 24 is in the left position, such as shown in FIG. 2. An indicium "L" is provided on the upper section of the bridge adjacent that slot 22E to indicate the left position.

Each of the transverse arms 26 and 28 is an elongated member which is mounted on the longitudinal arm 24 so that each transverse arm extends perpendicularly to the longitudinal axis 24D of the extending portion 24B of the arm 24. Each transverse arm is arranged to be located at a multitude of various discrete positions along the length of the longitudinal arm 24 by means (to be described later). Moreover, each transverse arm 26 and 28 is arranged to be rotated about a rotation axis with respect to the longitudinal arm 24. To that end, transverse arm 26 is arranged to be rotated about axis 26A and transverse arm 28 is arranged to be rotated about axis 28A, as best seen in FIGS. 1 and 6. The transverse arm 26 serves to mount one anatomy engagement component, e.g., a bite tray 36 (FIGS. 2-5), while the transverse arm 28 serves to mount another anatomy engagement component, e.g., a nasion pad 38 (FIGS. 2-5). To that end, a bite-tray mounting subassembly 40 is mounted on the transverse arm 26 and a bite-tray mounting subassembly 42 is mounted on the transverse arm 26. The details of the subassemblies 40 and 42 will be described in detail later.

Each of the transverse arms 26 and 28 is mounted on the elongated portion 24B of the longitudinal arm 24 via a respective interface piece 44 (FIGS. 2, 6, and 9-11). The interface piece 44 includes a portion 44A (FIG. 10) which is arranged to be disposed within a slot 46 (FIGS. 3, 1 and 9) extending longitudinally down substantially the length of the extending portion 24B of the longitudinal arm 24 and centered on axis 24D so that the interface piece 44 can be slid down that slot to any desired position therealong. A pair of a short series of undulations 48 is located above and below the portion 44A of the interface piece 44. The short strips of undulations 48 are arranged to engage any portion of a pair of long series of undulations 50. The long series of undulations 50 extend on the inner surface of the portion 24B of the arm 24 above and below the slot 46 and serve to enable the interface piece 44 to be located at any one of a myriad of discrete positions along the length of the arm 24. A tightening knob 52 having an associated screw (not shown), which when tightened, serves to pull the undulations of the strips 48 and 50 together to lock the interface piece 44 and the transverse arm 28 mounted thereon at the desired discrete position on the arm 24. In a similar manner a tightening knob 54 having an associated screw 56 (FIG. 9), which when tightened, serves to pull the undulations of the strips 48 and 50 together to lock the interface piece 44 and the transverse arm 26 mounted thereon at the desired discrete position on the arm 24. The longitudinal position of each of the transverse arms 26 and 28 on the longitudinal arm is designated by indicia 24C extending along the top surface of the extending portion 24B of the arm 24.

Figures 9, 10, 11, 12:
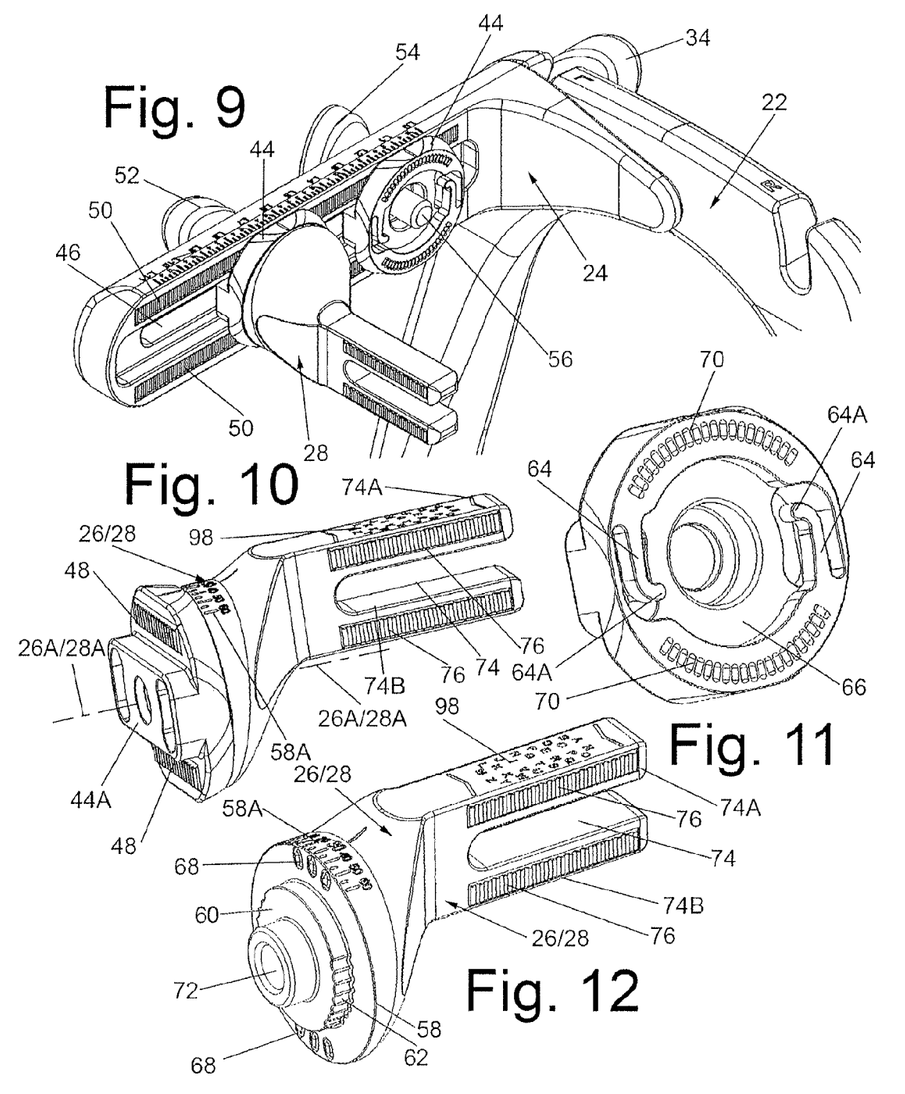
FIG. 9 is an isometric view of upper portion of the device in the state shown in FIG. 2 but with various components removed to illustrate the manner of mounting the transverse arms on the longitudinal arm.
FIG. 10 is an enlarged isometric view of a portion of the components shown in FIG. 9, i.e., an interface piece and a transverse arm coupled thereto.
FIG. 11 is an enlarged isometric view of the interface piece shown in FIGS. 9 and 10.
FIG. 12 is an isometric view of the transverse arm shown in FIGS. 9 and 10.

As mentioned earlier, the transverse arms 26 and 28 are arranged to be rotated about their respective axes 26A and 28A. To that end, as best seen in FIG. 12, each arm 26 and 28 includes an inner or proximal end portion 58 in the form of a circle and having a circular central boss 60. The boss includes a series of notches or grooves 62 extending along diametrically opposed sides of the boss. These notches cooperate with a pair of spring-biased fingers 64 in the interface piece 44 to enable the transverse arm to be rotated about its rotational axis with respect to the interface piece. In particular, the boss 60 fits within a corresponding shaped recess 66 (FIG. 11) in the front face of the interface piece 44. Each finger 64 includes a rounded free end 64A, which is arranged to be disposed in any of the grooves 62 when the transverse arm is manually twisted about its rotational axis. Thus, those cooperating members form a detent-mechanism, wherein the bias provided by the fingers holds the arm in its rotational orientation. However, that bias by can be readily overcome by the user twisting the arm in the desired rotational direction to bring the arm to another desired rotational orientation.

As best seen in FIGS. 11 and 12 the inner surface of the circular portion 58 of each transverse arm includes three rounded projections 68 disposed above and below the boss 60 and roughly ninety degrees from the position of the notches 62. The projections 60 are arranged to be received in any of a series of recesses 70 disposed in an arc on opposite sides of the circular recess 66 and roughly ninety degrees from the position of the fingers 64. In order to lock the transverse arm 28 in the desired rotational orientation the knob 54 is tightened. This action causes the screw 56, which is threadedly engaged in a threaded bore 72 (FIG. 12) on the arm 26, to pull the arm towards the interface piece 44, whereupon the projections 68 are tightly disposed within those recesses 70 which are disposed opposite the projections, thereby releasably locking the arm in the desired rotational orientation. Thus, it should be appreciated that the single knob 54 performs two functions, namely, when loosened it enables the transverse arm 26 to be moved to any desired discrete longitudinal position along the longitudinal arm 24 while enabling the transverse arm to be rotated about its rotational axis. When the knob 54 is tightened it locks the transverse arm 26 in that position and orientation. It should also be appreciated by those skilled in the art, that when the knob 54 is loosened the transverse arm will still be held in its rotational orientation by the heretofore described detent mechanism. Indicia 58A (FIGS. 6, 10 and 12) are provided on the outer surface of the portion 58 of the arms 26 and 28 to provide a visual indication of the angular orientation of those arms. The transverse arm 28 is constructed and mounted on the longitudinal arm 24 in an identical manner and its positioning and orientation controlled by a single knob 52.

As best seen in FIGS. 10 and 12 the distal or outer portion of the transverse arms 26 and 28 are each in the form of a fork having a linear slot 74 extending to the free end of the arm between the fork's linear tines 74A and 74B. That slot enables the mounting of the subassemblies 40 and 42 on the arms 26 and 28, respectively, by sliding the subassemblies into the slot on their respective arms.

The forked end of each transverse arm is laterally offset from the arm's axis of rotation as best seen in FIG. 10. In particular the lower tine 74B of the arm 26 is disposed above the rotation axis 26A, while the lower tine of the arm 28 is disposed above the rotation axis 28A. The offsetting of the distal ends of the transverse arms 26 and 28 provides more area underneath them when those arms are in their normal operative position, like shown in FIGS. 1 and 5, without necessitating increasing the height of the bridge member 22.

Figure 13:
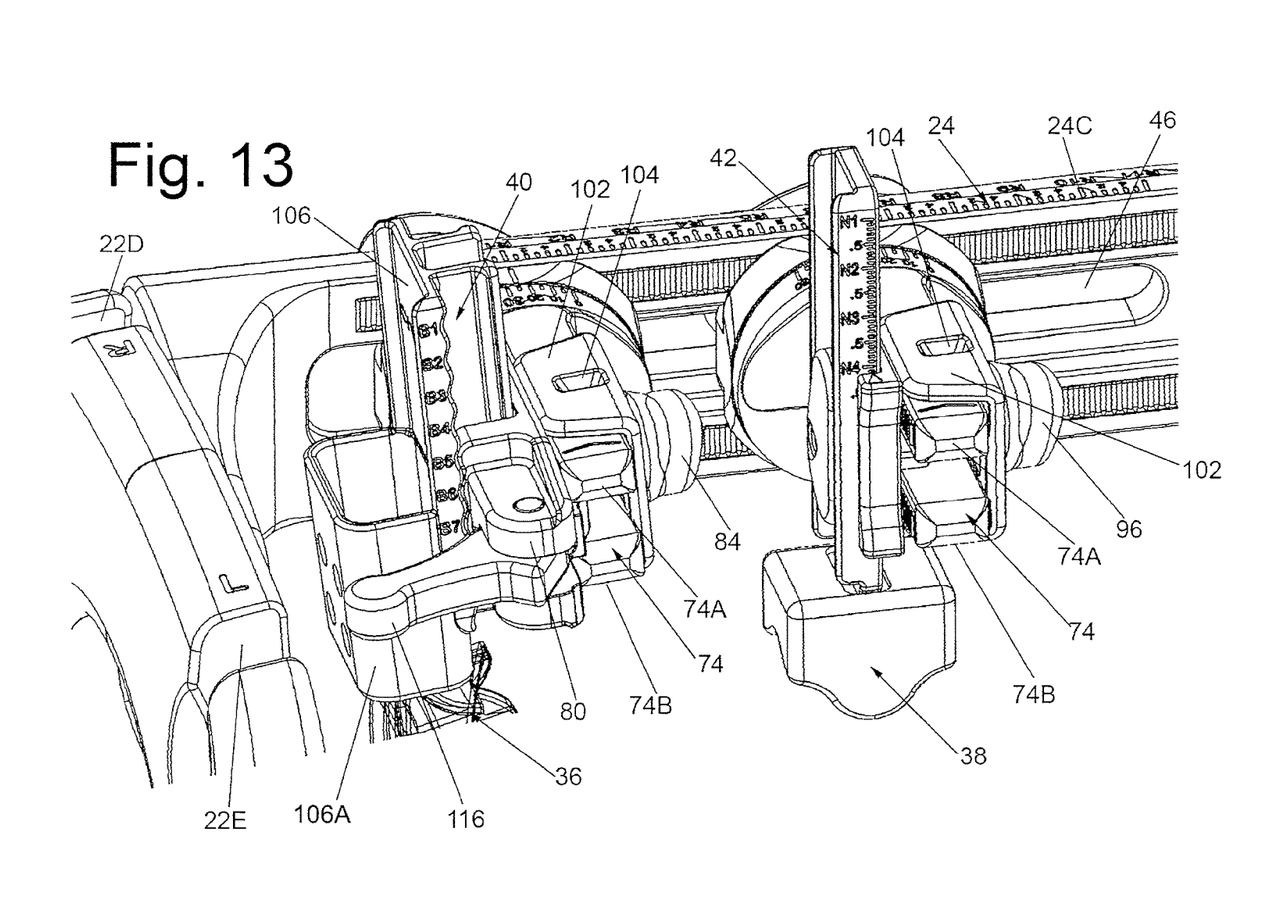
FIG. 13 is an enlarged isometric view of the device in the state of FIG. 6 and showing some details of the subassemblies mounting the nasion and the bite tray on their respective transverse arms.
Figure 14:
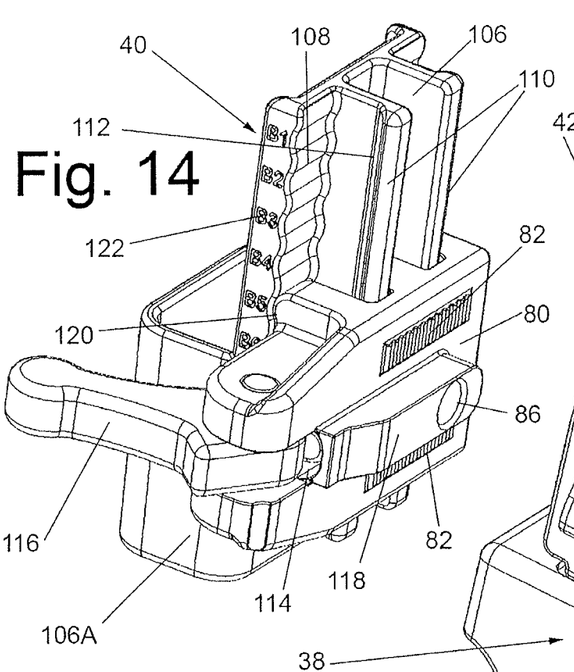
FIG. 14 is an enlarged isometric view of a portion of the subassembly mounting the bite tray onto its transverse arm.
Figure 15:
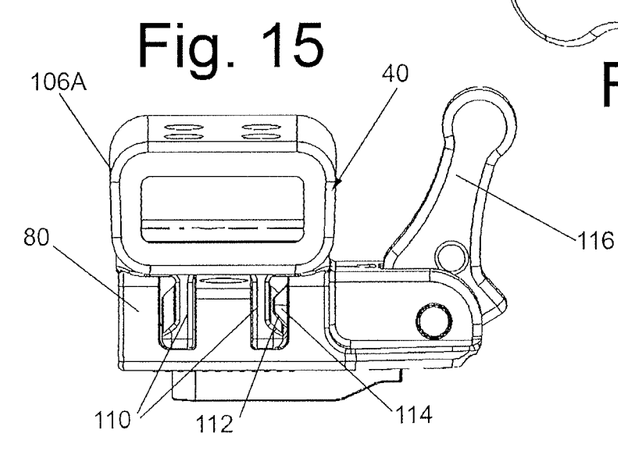
FIG. 15 is a top view of the portion of the subassembly shown in FIG. 14.

The tines 74A and 74B of each transverse arm includes a strip of undulations 76 on both the inferior and superior side of each tine. The strips of undulations 76 are similar to the strip of undulations 50 on the longitudinal arm 24. The undulation strips 76 on the tines are arranged to be engaged by portions of the subassemblies 40 and 42 having similar strips of undulations thereon. In particular, as best seen in FIG. 14 the subassembly 40 includes a first member 80 and a second member 106 (to be described later). The second member 106 serves as a carrier for mounting the bite tray 28 at the bottom thereof. The first member 80 has a rear surface on which two strips of undulations 82 are located. Those undulations are arranged to engage the undulations 76 on the tines 74A and 74B on either the superior side of the arm 26 or on the inferior side of that arm. A tightening screw (not shown) having a knob 84 (FIGS. 1 and 13) at its free end extends into engagement with a threaded bore 86 in a latch assembly (to be described later) coupled to the member 80. When tightened the knob 84 pulls the undulations 76 into tight engagement with the undulations 82, thereby locking the subassembly 40 at the desired lateral position along the arm 26.

Figure 16:
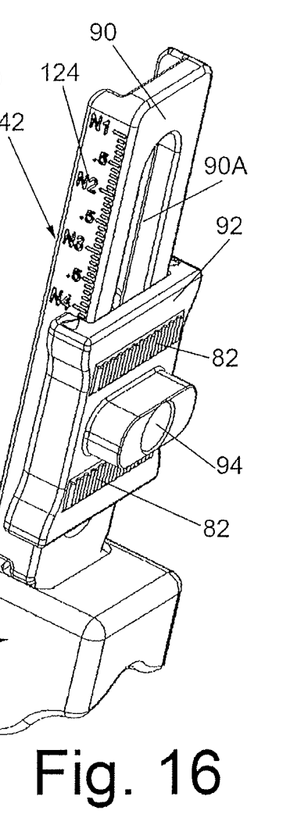
FIG. 16 is an enlarged isometric view of a portion of the subassembly mounting the nasion pad onto its transverse arm.

As best seen in FIG. 16, the subassembly 42 includes a first member 90 and a second member 92. The member 90 serves as a carrier mounting the nasion pad 38 at the bottom thereof. The second member 92 is in the form of a bracket for slidably mounting the carrier 90 and has a threaded bore 94 on one face thereof. The bracket 92 has a rear surface on which is disposed two strips of undulations 82 like those on member 80. The undulations 82 on the bracket 92 are arranged to engage the undulations 76 on the tines 74A and 74B on either the superior side of the arm 26 or on the inferior side of that arm. A tightening screw (not shown) having a knob 96 (FIGS. 1 and 13) at its free end extends through a bore 94 and into engagement with an internally threaded member 88 (FIG. 13) on the opposite of the carrier 90 so that when the knob is tightened it pulls the undulations 76 into tight engagement with the undulations 82, thereby locking the subassembly 42 at the desired position along the arm 28.

The position of the subassemblies 40 and 42 on the arms 26 and 28 respectively are indicated by indicia appearing on those arms. In particular, as best seen the upper surface of the tine 74A of the transverse arm 26 includes indicia 98 extending along the superior and inferior sides of that arm. Similar indicia are provided on the upper surface of the tine 74A of the transverse arm 28. In the exemplary embodiment shown the indicia represent the letters A-Z of the alphabet, with the letters forming four rows and being staggered in location along the upper surface of the tine 74A. A cover 102, having a window 104, forms a portion of the subassembly 40 and a similar cover forms a portion of the subassembly 42. The cover 102 moves with its subassembly along the transverse arm on which the subassembly is mounted. Moreover, the window 104 is oriented such that when the subassembly is mounted on either the superior or inferior side of its associated transverse arm at some particular longitudinal position therealong a respective letter from A to Z will appear in the window indicating that placement. For example, in the exemplary embodiment shown in FIG. 7 the indicia appearing in the window is the letter G, thereby revealing to the user that the subassembly 42 is at the longitudinal position G and on the superior side of the arm 28. If the subassembly 40 is at the same longitudinal position on the arm 26, but on the inferior side the indicia appearing in the window will be the letter T. Thus, the organization of the indicia coupled with the position of the window 104 provides the user with information relating to not only the longitudinal position of the subassembly on the arm, but also which side of the arm the subassembly is mounted on.

As mentioned previously, each subassembly 40 and 42 is arranged to enable the anatomy engaging component mounted thereon to be adjusted toward and away from the treatment table 12 or couchtop and hence the head of the patient. The details of the features to enable such adjustment will now be discussed first with respect to the subassembly 40 and then with respect to the subassembly 42. Turning now to FIG. 14, it can be seen that the subassembly 42 includes the heretofore identified carrier member 106 having the bite cup 106A at its lower end. The bite cup 106A is arranged to receive the flange (not shown) of the bite tray 36, with the flange of the bite tray being held in place in the bite cup by putty. The upper end of the carrier 106 is an elongate body having a rear surface including a series of undulations 108 and a pair of projecting rails 110 extending along the rear surface. Each rail includes a flanged free end in the form of a cam surface 112. The cam surface 112 is arranged to be engaged by a cam member 114 forming a portion of the heretofore mentioned latch assembly. That latch assembly is an over-center locking lever mechanism which includes a lever arm 116 and a member 118 in which the threaded bore 86 is located. The heretofore identified member 80 includes a front surface 120 which is undulated, like the undulations 108. The carrier 106 is arranged to be moved up and down with respect to the member 80, which is secured to the transverse arm 26, with the undulations of the surface 108 sliding over the undulations 120 of the member 80 when the lever arm of the latch assembly is in the open position. In the open position the lever arm 116 is rotated counter-clockwise from the position shown in FIG. 14 (i.e., the locked position). Rotating the lever arm to the closed or locked position, i.e., the position shown in FIG. 14, causes the cam member 114 to bear against the flanged surface 112. This action applies a force in two orthogonal directions, i.e., perpendicular to the plane of the rail 110 and parallel to the plane of the rail, thereby locking the undulations 108 and 120 together and locking the carrier 106 in that vertical position. The carrier 106 also includes indicia on its side adjacent the undulations 108 to provide an indication of the vertical position of the bite tray 36 with respect to the transverse arm 26. The vertical positioning of the nasion pad by the subassembly 42 on the transverse arm 28 will now be discussed. To that end the carrier 90, which mounts the nasion pad at the bottom thereof, is slidably disposed within the bracket 92 and thus can be moved therealong to any desired position. The heretofore identified tightening knob 96 effects the locking/unlocking of the carrier 90. In particular, the screw extending from the knob 96 passes through bore 94 in the bracket 92 and through a vertically extending slot 90A in the carrier 90 into threaded engagement with the member 88 on the opposite side of the carrier, thereby sandwiching the carrier 90 between the bracket 92 and the member 88. When the know 96 is tightened that lightly squeezes the carrier between those components, thereby fixing the carrier in the set position. Thus the use of the single knob 96 effects the locking of the subassembly at the desired transverse position along transverse arm 28 and also locks the carrier 90 at its desired height above the treatment table. In contradistinction, the knob 84 of the subassembly 40 merely effects the locking of that subassembly at the desired transverse position on its transverse arm 26. The locking of the carrier 106 of the subassembly 40 is effected by the heretofore described latch mechanism. The carrier 90 of the subassembly 42 also includes indicia 122 on its side to provide an indication of the vertical position of the nasion pad 38 with respect to the transverse arm 28.

As discussed above, the subassemblies 40 and 42 are arranged to be located at various discrete positions along the length of the arms 26 and 28, respectively and on either the superior or inferior side of the arm. Moreover, each subassembly is arranged to be mounted on its transverse arm so that when the longitudinal arm is in the opposite position from the desired operative position, the subassemblies will be facing upward, such as shown in FIG. 2 to expedite mounting of nasion and bite tray on their respective subassemblies. Then the arm 24 can be rotated 180 degrees to the opposite (and desired) position, whereupon the subassemblies will be oriented facing downward toward the patient's head, such as shown in FIG. 1 and any final positioning of the nasion and bite tray accomplished, if necessary.

Figure 17:
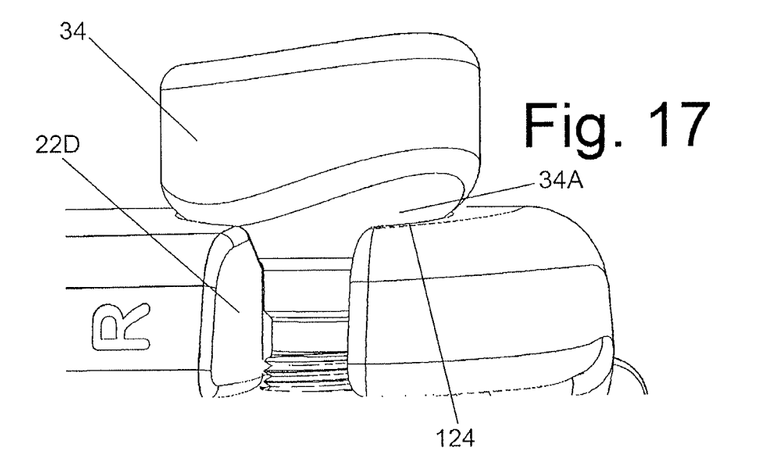
FIG. 17 is an enlarged top plan view of a portion of the device shown in FIG. 1 and showing the cooperating features of a locking knob and a recess in the bridge member or arch that pivotably mounts the longitudinal arm thereon to ensure that the longitudinal arm is in the precise position on the right side of the bridge member or arch.
Figures 18, 19:
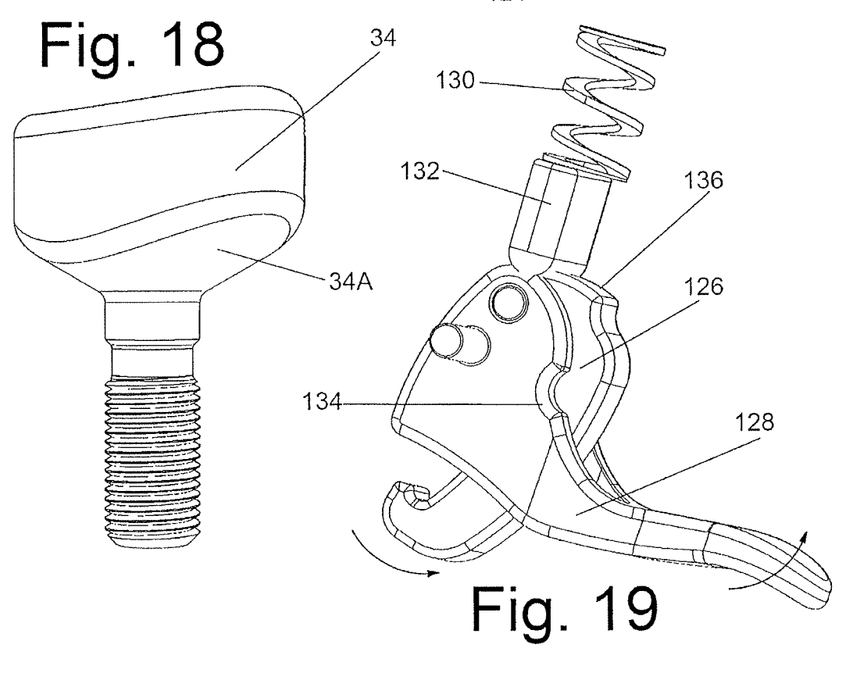
FIG. 18 is a plan view of the entire locking knob shown in FIG. 17.
FIG. 19 is an enlarged isometric view of one of the latch mechanisms for releasably mounting the associated leg of the bridging member or arch onto a treatment table (e.g., couchtop) or base (it being understood that each leg includes its own latch mechanism).

In order to ensure that when the arm 24 is in either the right or left position on the bridge its extending portion 24B is oriented parallel to the treatment table and a desired distance therefrom, the knob 34 is particularly configured so that it will fit within a mating recess at the desired slot to achieve that result. In particular, as best seen in FIGS. 17 and 18 the knob 34 includes a conical rear surface 34A which is arrange to be located within a correspondingly shaped conical recess 124 contiguous with the slot 22D or within a correspondingly shaped recess 124 contiguous with the slot 22E. The recesses 124 are each at the same height with respect to the treatment table or couchtop on which the device is mounted.

The releasable mounting of the device 20 on the treatment table, couchtop or base, as mentioned above, is accomplished by means of the latch assembly 30. That assembly is shown in FIG. 19 in its locked position, i.e., when its latch (to be described shortly) is within the notch or slot 10 of the treatment table or base and in engagement with the undersurface of thereof, thereby locking the device onto the treatment table or base. The latch assembly is an over-center mechanism which basically comprises a generally C-shaped latch 126, a pivotable lever 128, a biasing spring 130 and a detent slide 132. The pivotable lever includes a front or yoke portion having a pair of opposed sidewalls defining a space therebetween in which the latch is pivotably mounted. Each sidewall of the yoke includes a detent-receiving recess 134. Each latch mechanism 30 is located within a respective cavity in the bottom of its associated bridge leg 22A or 22B. The upper surface 136 of the latch is arranged to cooperate with a portion, e.g., a lip, of the interior of the cavity of the device leg so that the portion, e.g., lip, bears against the surface 136 when the latch is in the locked position, like shown in FIG. 19. In order to open or release the latch the lever 128 is lifted up (rotated in the counterclockwise direction as shown by the arrow adjacent the lever in FIG. 19), which action causes the latch to pivot outward (rotate in the counterclockwise direction as shown by the arrow adjacent the latch in FIG. 19) and the detent slide 132 to enter into the recesses 134, thereby holding the lever and latch in the unlocked position. This is the position that the latch mechanism will be in to attach the device 20 to the treatment table or base 12. To that end, the device 20 is placed on the treatment table or base 12 so that its open latches 126 enter into the notches or slots 10 in the treatment table or base. Then the lever 128 is pushed downward (i.e., in the clockwise direction in FIG. 19), whereupon the bias provided by the spring is overcome so that the detent slide 132 moves out of the recesses 134 and the latch 126 swings inward (i.e., in the clockwise direction in FIG. 19). At this time the geometry, i.e., the lip, in the cavity of the leg in which the latch mechanism is mounted acts on the latch surface 136 tensioning the latch upward, whereupon the bottom of the latch engages the undersurface of the treatment table or base contiguous with the notch or slot 10, thereby locking the device 20 in place on the treatment table 12.

As should be appreciated by those skilled in the art the device of this invention exhibits the following important features. The longitudinal arm 24 is attached pivotally to the main arch frame (bridge member) to facilitate left-right flipping, and vice versa, without removal of the arm. Mating surfaces, e.g., conical geometry, is employed to ensure proper position of longitudinal arm when secured in place. The transverse arms 26 and 28 are positionally secured longitudinally and in rotation about their longitudinal axis, each with a single knob. Those transverse arms each employ a spring loaded detent mechanism which helps find the discreet rotational positions and keeps the rotational adjustment and longitudinal adjustments separate. Moreover, the transverse arms are capable of 360 degree rotation without removal (again enhancing flipping from the left to right, and vice versa, orientation without requiring disassembly of components. Further still, the transverse arms are configured with an open end (e.g., like a fork) to facilitate removal and re-attachment of the bite tray and nasion mounting subassemblies, with minimal disassembly. Further yet, the bite cup carrier has discreet registration positions achieved via multiple engaging undulations. The longitudinal movement and lateral adjustment of the transverse arms make use of substantial multiple small cooperating undulations to establish discrete positions, while minimizing wear. The bite cup carrier comprises an over-center locking lever mechanism securing the bite tray carriage in two distinct perpendicular horizontal directions, whereupon release of the locking mechanism releases securement from both directions if the bite tray has to be disengaged from the patient for safety reasons. The transverse arms include indicia (nomenclature/labeling) indicating the lateral position as well whether or not the nasion or the bite cup is inferior or superior with respect to the transverse arm and include nonnumeric or lettering graphics indicating the lateral center position. The locking lever/latch system for mounting the device on a couchtop or some other base enables that action to be accomplished as a one-step function. Moreover, the base locking lever/latch system includes means in the form of a detent positioner allowing the user to initially position the device on a storage base or lift it clear of the base once released without requiring the manipulating or holding of any levers or latches.

Without further elaboration the foregoing will so fully illustrate our invention that others may, by applying current or future knowledge, adopt the same for use under various conditions of service.

We claim:
1. A device for positioning and immobilizing the head of patient on a treatment table for some type of therapy, the treatment table having a longitudinal axis, said device comprising a bridge member, a first arm, and at least a second arm, said bridge member being a generally U-shaped member having an upper, central portion and a pair of elongated side legs, said upper, central portion having one side located immediately adjacent one of said side legs and another side located immediately adjacent the other of said side legs, said bridge member being arranged to be mounted on the treatment table with said side legs extending generally perpendicularly to the treatment table and with said upper, central extending transversely above the head of the patient, whereupon the head of the patient is interposed between said upper, central portion and the treatment table, said first arm being an elongated member having a first longitudinal axis, said first arm being pivotably mounted on said upper, central portion of said bridge member and so that said first longitudinal axis extends parallel to the longitudinal axis of the treatment table and above the patient's head, said first arm being arranged to be pivoted from one side of said upper, central portion of said bridge member to the other side of said upper, central portion of said bridge member, and vice versa, whereupon said first arm can be located with said first longitudinal axis extending parallel to the longitudinal axis of the treatment table above either side of the patient's head, said second arm being an elongated member having a second longitudinal axis, said second arm being releasably secured to said first arm whereupon said second longitudinal axis extends transversely to said first longitudinal axis, said second arm being positionable along a portion of the length of said first arm and arranged to mount an anatomy engagement component thereon for engaging a portion of the anatomy of the patient's head.

2. The device of claim 1 wherein said second arm is rotatable about said second longitudinal axis.

3. The device of claim 2 additionally comprising a spring-loaded detent mechanism for enabling said second arm to be manually rotated about said second longitudinal axis to a desired angular orientation with respect thereto and to hold said second arm in said desired orientation.

4. The device of claim 3 additionally comprising a knob arranged to be tightened or loosened, which when loosened enables said second arm to be rotated about said second longitudinal axis to said desired orientation and which when tightened enables said second arm to be secured in said desired orientation.

5. The device of claim 4 wherein said spring loaded detent mechanism comprises a portion of an interface member, said interface member being interposed between said first arm and said second arm, said interface member having a series of small recesses extending in an arc across a portion of said interface member, said second arm having an inner end portion having a series of small projections extending in an arc across said inner end portion, said series of small projections of said second arm being arranged to engage portion of said series of small recesses of said interface member by the tightening of said knob to thereby releasably lock said second arm in said orientation.

6. The device of claim 2 wherein said second arm comprises a superior surface and an inferior surface and wherein said device additionally comprises a subassembly for mounting an anatomy engaging component at any of a series of discrete positions on either said superior surface or inferior surface of said second arm, said device additionally comprising indicia on said second arm indicating the discrete position of said subassembly on said second arm and whether the subassembly is on said superior surface or said inferior surface.

7. The device of claim 6 wherein said subassembly includes a cover member having a window therein arranged to expose one of said indicia indicative of the discrete position of said subassembly on said second arm and whether the subassembly is on said superior surface or said inferior surface.

8. The device of claim 2 wherein said second arm comprises a superior surface and an inferior surface and wherein said device additionally comprises a subassembly for mounting an anatomy engaging component on either said superior surface or inferior surface of said second arm, said superior surface of said arm and said inferior surface of said arm each including a series of small undulations extending across a major portion thereof, said subassembly including a portion having a series of small undulations extending thereacross, said series of small undulations of said second arm being arranged to engage portion of said series of small undulations of said portion of said subassembly establish discrete positions of said subassembly along the length of said second arm.

9. The device of claim 8 wherein said subassembly comprises a first member having an undulating surface, a second member having a mating undulating surface, and a latching mechanism, said first and second members being movable with respect to each other by said latching mechanism to cause said undulating surfaces to releasably engage each other, said first undulating surface being arranged to be moved along said second undulating surface to adjust the position of said anatomy engaging component toward or away from the treatment table.

10. The device of claim 2 wherein said second arm has a superior surface and an inferior surface and wherein said second arm includes a forked distal end enabling the mounting of said anatomy engagement component on either said superior surface or inferior surface of said second arm.

11. The device of claim 10 wherein said device additionally comprises a subassembly for mounting said anatomy engaging component on either said superior surface or inferior surface of said second arm, said subassembly being arranged to adjust the position of said anatomy engaging component toward or away from the treatment table.

12. The device of claim 1 additionally comprising a knob arranged to be tightened or loosened, which when loosened enables said second arm to be slid to a desired position along a portion of the length of said first arm and which when tightened enables said second arm to be secured in said desired position.

13. The device of claim 1 additionally comprising an interface member interposed between said second arm and said first arm, said interface member having a series of small undulations extending across a portion of said interface member, said first arm having a series of small undulations extending along a major portion thereof, said series of small undulations of said interface member being arranged to engage portion of said series of small undulations of said first arm to establish discrete positions of said second arm along the length of said first arm, said undulations being arranged to be brought into releasable securement by the tightening of said knob to thereby releasably lock said second arm in said desired position.

14. The device of claim 1 additionally comprising a third arm, said third arm being an elongated member having a third longitudinal axis, said third arm being releasably secured to said first arm whereupon said third longitudinal axis extends transversely to said first longitudinal axis, said third arm being positionable along a portion of the length of said first arm and arranged to mount another component for engaging a portion of the anatomy of the patient's head.

15. The device of claim 14 wherein said third arm is rotatable about said third longitudinal axis.

16. The device of claim 12 additionally comprising a first knob and a second knob, each of said knobs being arranged to be tightened or loosened, said first knob when loosened enables said second arm to be slid to a desired position along a portion of the length of said first arm and when tightened enables said second arm to be secured in said desired position, said first knob when loosened enables said second arm to be rotated about said second axis to a desired orientation and when tightened enables said second arm to be secured in said desired orientation, said second knob when loosened enables said third arm to be slid to a desired position along a portion of the length of said first arm and which when tightened enables said third arm to be secured in said desired position, said second knob when loosened enables said third arm to be rotated about said third axis to a desired orientation and which when tightened enables said third arm to be secured in said desired orientation.

17. The device of claim 16 additionally comprising a first spring-loaded detent mechanism for enabling said second arm to be manually rotated about said second axis to a desired angular orientation with respect thereto and to hold said second arm in said desired orientation and a second spring-loaded detent mechanism for enabling said third arm to be manually rotated about said third axis to a desired angular orientation with respect thereto and to hold said third arm in said desired orientation.

18. The device of claim 15 wherein said second arm has a superior surface and an inferior surface and wherein said second arm includes a forked distal end enabling the mounting of an anatomy engagement component on either said superior surface or inferior surface of said second arm and wherein said third arm has a superior surface and an inferior surface and wherein said third arm includes a forked distal end enabling the mounting of another anatomy engagement component on either said superior surface or inferior surface of said third arm.

19. The device of claim 18 wherein said device additionally comprises a first subassembly and a second subassembly, said first subassembly being arranged for mounting said anatomy engaging component on either said superior surface or inferior surface of said second arm, said first subassembly being arranged to adjust the position of said anatomy engaging component toward or away from the treatment table, said second subassembly being arranged for mounting said another anatomy engaging component on either said superior surface or inferior surface of said third arm, said second subassembly being arranged to adjust the position of said another anatomy engaging component toward or away from the treatment table.

20. The device of claim 9 wherein said latching mechanism releasably secures said first and second members of said subassembly in two perpendicular directions lying in plane generally parallel to the treatment table and wherein the release of said latching mechanism causes the immediate release of said first and second members of said subassembly from both perpendicular directions.

21. The device of claim 1 wherein said upper, central portion of said bridge member includes a pair of slots, one of said slots being located adjacent one side of said upper portion of said bridge member, the other of said slots being located adjacent the opposite side of said upper portion of said bridge member, said device additionally comprising a member coupled to said first arm, said member including a portion adapted for disposition within either of said slots to precisely locate said first arm in a desired orientation with respect to the treatment table.

22. The device of claim 1 wherein the treatment table includes an undersurface and wherein said device additionally comprises an over-center latch mechanism arranged to releasably mount said device on the treatment table by causing a latch of said latch mechanism to engage and bear upon said undersurface.

* * * * *